United States Patent
Kowol

[11] 3,958,935
[45] May 25, 1976

[54] METHOD FOR DISINFECTING ROOMS AND ARTICLES THEREIN

[75] Inventor: Klaus Kowol, Lubeck, Germany

[73] Assignee: Drägerwerk Aktiengesellschaft, Germany

[22] Filed: May 9, 1974

[21] Appl. No.: 468,364

[30] Foreign Application Priority Data
June 30, 1973  Germany............................ 2333411

[52] U.S. Cl........................................ 21/58; 21/2; 21/53; 21/DIG. 1
[51] Int. Cl.$^2$...................... A61L 1/00; A61L 9/02; A61L 13/02
[58] Field of Search ............... 21/58, DIG. 1, 53, 2, 21/DIG. 3

[56] References Cited
UNITED STATES PATENTS

| | | | |
|---|---|---|---|
| 360,456 | 7/1907 | Fournier ................................ | 21/58 |
| 1,062,404 | 5/1913 | Kiefer .................................... | 21/58 |
| 1,114,880 | 10/1914 | Hall ....................................... | 21/110 |
| 1,837,264 | 12/1931 | Hackley ................................. | 21/58 |
| 3,547,576 | 12/1970 | Sheikh ................................... | 21/58 X |
| 3,816,074 | 6/1974 | Decupper........................ | 21/74 R X |

FOREIGN PATENTS OR APPLICATIONS

| | | | |
|---|---|---|---|
| 1,604,353 | 12/1971 | France ................................... | 21/58 |
| 2,081,231 | 3/1971 | France ................................... | 21/58 |
| 83,058 | 9/1895 | Germany ............................... | 21/58 |
| 737,893 | 10/1955 | United Kingdom.................... | 21/58 |

Primary Examiner—Morris O. Wolk
Assistant Examiner—Bradley R. Garris
Attorney, Agent, or Firm—McGlew and Tuttle

[57] ABSTRACT

A method and apparatus for disinfecting rooms and articles in the rooms. The apparatus comprises a housing having an interior disinfecting chamber which is connected through a valve to a scavenging chamber containing a scavenging fan, which has a discharge to atmosphere. An inlet chamber has an inlet valve which may be opened for the inflow of air through a filter into the inlet chamber and the disinfectant chamber. In addition, the housing contains a circulating fan chamber which is connected through an inlet passage having a plurality of circulating socket connections which extend from the circulating fan passage into the disinfectant chamber, and which may be advantageously connected selectively to articles which are to be disinfected. The discharge passage for the circulating fan which extends from the circulating fan passage into the disinfecting passage, passes over preferably at least one evaporator for the evaporation of the disinfectant and, preferably, two evaporators, one of which is an evaporator for a neutralizing agent for the disinfectant. In the method, disinfectant is added to the air in the disinfectant chamber to form a disinfectant gas which may advantageously be evaporated or atomized in the presence of air which is circulated into the chamber. The disinfectant gas is heated and circulated to disinfect the chamber and the articles therein and, thereafter, the disinfectant gas is exhausted from the chamber and air is circulated through the chamber to scavenge it. In a subsequent operation, the air in the chamber is heated in order to evaporate the residual disinfectant and after expiration of a predetermined period of time, this heated air is scavenged from the chamber by circulating fresh air therethrough.

3 Claims, 1 Drawing Figure

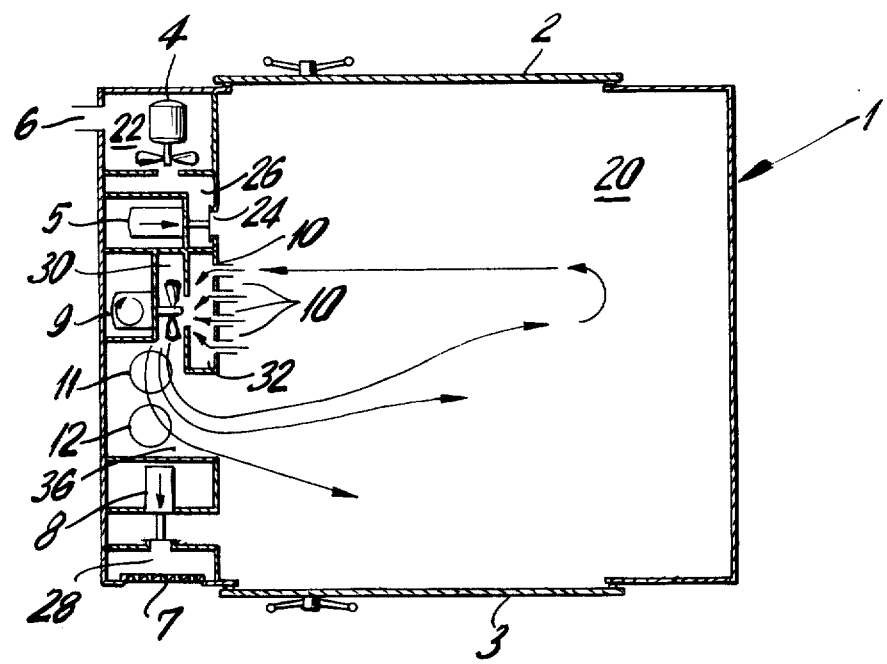

METHOD FOR DISINFECTING ROOMS AND ARTICLES THEREIN

BACKGROUND OF THE INVENTION

1. Field of the Invention

This invention relates in general to a method and apparatus for disinfecting chambers or rooms and, in particular, to a new and useful method and apparatus for disinfecting rooms or chambers and articles therein, particularly disinfecting chambers having drying rooms having protective breathing apparatus, medical devices or similar articles.

2. Description of the Prior Art

It is known to disinfect articles such as protective breathing apparatus by placing them in a so-called disinfecting chamber. The disinfecting chamber is equipped with an evaporation device for the disinfectant, for example, formaldehyde, and heating devices for warming the air in the chamber. After the objects are placed in the chamber, the disinfectant is evaporated, and the air in the chamber is warmed up. It is also known to first warm the chamber and then to put the evaporator for the disinfectant into operation. It is further known to circulate air in the chamber during the disinfection in order to bring all of the parts located in the chamber into contact with the disinfectant vapors or atomized articles to kill the germs. Subsequently, the chamber is scavenged with fresh air.

Use of formaldehyde as a disinfectant is also known. Formaldehyde is a very good disinfectant, but it has the disadvantage that it has a sharp and very annoying odor. Since the formaldehyde adheres to the objects to be disinfected, the handling of these objects is in many cases difficult.

Ammonia has been used for binding the formaldehyde. The disadvantage of such an operation is that, while binding formaldehyde with ammonia, urotropin is produced which is deposited on the surface of the objects to be disinfected. For many reasons, such a deposit is undesirable. Even though harmless and easily soluble in water, urotropin must be wiped off in many cases. It is also disadvantageous because urotropine constantly releases small quantities of formaldehyde.

Placing articles which are to be disinfected into rooms which are provided with an evaporation device for formaldehyde and an evaporation device for ammonia and which include an air conveying device for circulating in the room are also known, but all of the known devices operate as indicated above.

SUMMARY OF THE INVENTION

The invention provides a simple disinfecting process which may be carried out in order to ensure that no disinfectant, such as formaldehyde, adheres to the objects to be disinfected and that as far as possible, an additional binding of the disinfectant with other agents, such as formaldehyde with ammonia, will not be possible. With the invention, the disinfectant chamber is designed so that an additional operational step may be carried out wherein the residual disinfectant is evaporated, the air in the room is warmed up and circulated and, after an expiration of a predetermined period of time, the chamber is scavenged with fresh air.

The process of the invention has the advantage that the residual quantities of the disinfectant which still adhere to the particles to be disinfected after scavenging of the room with fresh air are evaporated during the additional circulation and warming up of the air and they are absorbed in the heated air and after an expiration of a predetermined time are scavenged out of the room. Thus, at an increased temperature and thereby increased gas pressure of the disinfectant, such as formaldehyde, the disinfectant diffuses even from porous surfaces of the objects to be disinfected and mixes with the air in the room. Thereby, residual disinfectant is removed more rapidly and the annoying smell, eye irritation, etc., is avoided.

Even for objects having a particularly complicated surface, due either to porous materials or to multiple-surface design, this method may be used advantageously if the process is repeated several times.

According to another feature of the invention, even after the scavenging, the air in the room may be enriched with a binding agent or decomposing agent which reacts with the disinfectant and the products may be subsequently scavenged.

Since with the process according to the invention, only small quantities of disinfectant can remain which adhere to the objects to be disinfected, only a correspondingly small quantity of the substance binding the disinfectant is used.

An apparatus which is used particularly for carrying out the invention includes not only an inlet chamber with an inlet valve control passage and a scavenging chamber with a scavenging pump and a valve control, but also a circulating chamber with a passage in which are located an evaporator for the disinfectant and an evaporator for an agent.

Accordingly, it is an object of the invention to provide an improved process for disinfecting chambers and articles in the chambers wherein disinfectant is added to air circulated through the chamber to form a disinfectant gas which is advantageously heated and circulated to disinfect the room and the articles therein and thereafter exhaust it and scavenging air is circulated through the chamber to facilitate the exhaustion of the residue; and wherein, in a subsequent operation, the air in the chamber is heated to evaporate the residual disinfectant and after a predetermined period of time, the room is scavenged a second time by circulating fresh air therethrough.

A further object of the invention is to provide an apparatus for carrying out the method which includes a housing having an opening at each side which is closed by removable covers for the introduction and removal of articles, and which also includes an inlet passage having a valve control and a circulating fan chamber having a discharge for the scavenged gases and a connecting passage which leads into the disinfecting chamber and is controlled by a valve, and which also includes a circulating fan chamber having a plurality of inlet sockets connected into the disinfecting chamber and a discharge passage having an evaporator for a disinfectant substance and an evaporator for a neutralizing agent.

A further object of the invention is to provide a device which is simple in design, rugged in construction, and economical to manufacture.

The various features of novelty which characterize the invention are pointed out with particularity in the claims annexed to and forming a part of this disclosure. For a better understanding of the invention, its operating advantages and specific objects attained by its uses, reference should be had to the accompanying drawing and descriptive matter in which there is illustrated a preferred embodiment of the invention.

BRIEF DESCRIPTION OF THE DRAWING

The only FIGURE of the drawing is a schematic horizontal sectional view of a disinfecting chamber constructed in accordance with the invention.

DESCRIPTION OF THE PREFERRED EMBODIMENT

Referring to the drawing in particular, the invention embodied therein, comprises a housing, generally designated 1, having an interior disinfectant chamber 20, which is adapted to receive articles which are to be disinfected and which is provided with openings at its respective opposite sides which are closed by removable covers 2 and 3, which may be easily opened in order to place articles into and out of the disinfecting chamber 20 as desired.

In accordance with the invention, housing 1 includes a scavenging fan chamber 22 adjacent one side which contains a scavenging fan 4 which, when operated, discharges gases from the interior of disinfectant chamber 20 through a discharge passage 6. The gases are removed from the chamber 20 through an opening 24 which is controlled by an automatic valve 5 arranged in an inlet passage 26 extending from the scavenging fan passage 22 to disinfectant chamber 20. Valve 5 is advantageously electromagnetically controlled.

A similar electromagnetically controlled valve 8 is arranged at an inlet chamber 28 and valve 8 may be opened to draw in fresh air through filter 7 through inlet passage 28 to the disinfectant chamber 20.

In accordance with the invention, a circulating fan chamber 30 is provided intermediate the width of housing 1 and it is provided with a circulating air inlet passage 32 which communicates through a plurality of connecting sockets 10 to the disinfecting chamber 20. The gases are circulated through the disinfectant chamber in the direction of the arrows indicated by the circulating fan 9 to cause the gases to move through inlet passage 32 and through a discharge connecting passage 36 which opens into disinfectant chamber 20. Circulating fan discharge connecting passage 36 is provided with an evaporator 11 for evaporating the disinfectant, such as formaldehyde, and in addition, it is provided with an evaporator 12 for evaporating a neutralizing agent, such as ammonia.

Connecting sockets 10 are advantageously provided for individually connecting articles to be disinfected thereto. The heating and evaporation device 11 comprises an evaporator 11 for the disinfectant which, in the present example, is formaldehyde, and the other evaporator 12 for the neutralizing agent, advantageously is operated with ammonia. Both evaporators 11 and 12 are provided with an electric heater.

The operation of the device is as follows:

Upon introduction of the devices into the disinfectant chamber 20, solenoid valves 5 and 8 are closed, and the evaporator 11, as well as circulating fan 9, are put into operation. The air in chamber 20 becomes enriched with the evaporated disinfectant and it is advantageously warmed up and circulated in the direction of the arrows indicated. After the disinfection is terminated, the evaporator 11 is cut off and the scavenging fan 4 is put into operation while valves 5 and 8 are opened. Fresh air is then taken in through the disinfecting chamber 20 and thereby, the formaldehyde is scavenged and passes with the air to the outside through outlet 6. Outlet 6 may, for example, be connected to a filter if necessary or desired.

Thereafter, valves 5 and 8 are closed and the disinfectant chamber is again scavenged with fresh air. In some instances, the air chamber may be enriched with a neutralizing agent by placing evaporator 12 into operation. This operation is carried out in the same manner as the disinfecting step.

In a subsequent operation, the air from chamber 20 is heated up by the heaters in either of evaporators 11 or 12, or by other heaters placed in room 20, to cause an evaporation of the residual disinfectant. After expiration of a predetermined period of time, the chamber 20 is scavenged by circulating fresh air therethrough. With this subsequent heating up of the air, the disinfectant is completely removed without an expenditure of a very great amount of energy.

While a specific embodiment of the invention has been shown and described in detail to illustrate the application of the principles of the invention, it will be understood that the invention may be embodied otherwise without departing from such principles.

What is claimed is:

1. In a method of disinfecting chambers and articles therein comprising the steps of adding disinfectant to the air in the chamber to form a disinfectant gas, heating and circulating the disinfectant gas to disinfect the chamber and the articles therein, circulating fresh air through said chamber thereby exhausting the disinfectant gas from the chamber and scavenging the chamber, the improvement comprising following said fresh air circulating step by at least one residual disinfectant scavenging sequence of steps consisting of (a) heating the air remaining in the chamber to evaporate the residual disinfectant and after an expiration of a predetermined period of time, (b) circulating fresh air through the chamber to scavenge the chamber.

2. In a method of disinfecting chambers and articles therein, according to claim 1, the improvement further comprising repeating said residual disinfectant scavenging sequence of steps.

3. In a method of disinfecting chambers and articles therein according to claim 1, the improvement further comprising enriching the air remaining in the chamber with a neutralizing gas after said residual disinfectant scavenging sequence of steps.

* * * * *